(12) United States Patent
Miyatani et al.

(10) Patent No.: US 10,966,730 B2
(45) Date of Patent: Apr. 6, 2021

(54) BONE RESECTION APPARATUS (71) Applicant: Miyatani Co., Ltd., Matsuyama (JP)

(72) Inventors: Naofumi Miyatani, Matsuyama (JP); Hirotsugu Muratsu, Kakogawa (JP)

(73) Assignee: Miyatani Co., Ltd., Matsuyama (JP)

( * ) Notice: Subject to any disclaimer, the term of this patent is extended or adjusted under 35 U.S.C. 154(b) by 117 days.

(21) Appl. No.: 16/529,856

(22) Filed: Aug. 2, 2019

(65) Prior Publication Data
US 2020/0375609 A1 Dec. 3, 2020

(30) Foreign Application Priority Data

May 27, 2019 (JP) .................................. JP2019-98176

(51) Int. Cl.
| | | |
|---|---|---|
| *A61B 17/14* | (2006.01) | |
| *A61B 17/15* | (2006.01) | |
| *A61B 17/16* | (2006.01) | |
| A61B 17/17 | (2006.01) | |
| A61B 17/32 | (2006.01) | |

(52) U.S. Cl.
CPC .......... *A61B 17/142* (2016.11); *A61B 17/154* (2013.01); *A61B 17/1604* (2013.01); *A61B 17/1659* (2013.01); *A61B 17/1728* (2013.01); *A61B 17/1764* (2013.01); *A61B 17/32002* (2013.01)

(58) Field of Classification Search
CPC ............................. A61B 17/14; A61B 17/142
See application file for complete search history.

(56) References Cited

U.S. PATENT DOCUMENTS

| | | | | |
|---|---|---|---|---|
| 5,735,866 A | * | 4/1998 | Adams ................ | B23D 61/006 30/339 |
| 6,656,186 B2 | * | 12/2003 | Meckel ............... | A61B 17/142 30/350 |
| 7,497,860 B2 | * | 3/2009 | Carusillo ............ | A61B 17/142 606/82 |
| 8,608,745 B2 | * | 12/2013 | Guzman ............. | A61B 17/142 606/82 |

(Continued)

FOREIGN PATENT DOCUMENTS

| | | |
|---|---|---|
| JP | 2007-532253 A | 11/2007 |
| JP | 2016-529952 A | 9/2016 |

(Continued)

*Primary Examiner* — Eric S Gibson
(74) *Attorney, Agent, or Firm* — JTT Patent Services, LLC; Gerald T. Peters (57) ABSTRACT

A bone resection apparatus may comprise a roughly planar blade body that has a tip saw blade and that carries out cutting of bone with which the tip saw blade makes contact as a result of high-speed oscillation; and a guide plate which has a roughly planar tip guide portion, which is located at a top side of the blade body, and which is connected in such fashion as to permit sliding in a front-and-back direction relative to the blade body, the guide plate being capable of sliding between a protruding guide state in which the tip guide portion is made to protrude toward the tip to a point beyond the tip saw blade of the blade body to cover the tip saw blade and to guide a location in a thickness direction at which cutting by the tip saw blade occurs, and a retracted guide state in which the tip guide portion is retracted to a point behind the tip saw blade.

7 Claims, 8 Drawing Sheets

(56) References Cited

U.S. PATENT DOCUMENTS

| | | | |
|---|---|---|---|
| 9,468,445 B2 * | 10/2016 | McGinley | A61B 17/320068 |
| 10,327,784 B2 * | 6/2019 | Guzman | A61B 17/142 |
| 10,687,824 B2 * | 6/2020 | Shiels | A61B 17/142 |
| 2003/0199880 A1 * | 10/2003 | Meckel | A61B 17/142 606/82 |
| 2004/0199167 A1 * | 10/2004 | Fletcher | A61B 17/142 606/79 |
| 2006/0009796 A1 * | 1/2006 | Carusillo | B27B 19/006 606/178 |
| 2007/0083209 A1 * | 4/2007 | Schenberger | A61B 17/142 606/82 |
| 2007/0123893 A1 * | 5/2007 | O' Donoghue | A61B 17/142 606/82 |
| 2008/0243125 A1 * | 10/2008 | Guzman | A61B 17/142 606/82 |
| 2010/0292701 A1 * | 11/2010 | Fisher | A61B 17/142 606/82 |
| 2014/0100577 A1 * | 4/2014 | Guzman | A61B 17/142 606/82 |
| 2014/0163558 A1 * | 6/2014 | Cosgrove | A61B 17/142 606/82 |
| 2014/0243832 A1 * | 8/2014 | Kelly | A61B 17/14 606/82 |
| 2015/0000143 A1 * | 1/2015 | Bozic | A61B 17/14 30/347 |
| 2018/0064447 A1 * | 3/2018 | Koljaka | A61B 17/142 |
| 2018/0064448 A1 * | 3/2018 | Mac an Tuile | A61B 17/14 |
| 2019/0021745 A1 * | 1/2019 | Shiels | A61B 17/142 |
| 2019/0192170 A1 * | 6/2019 | Nunan | A61B 17/142 |
| 2019/0336139 A1 * | 11/2019 | Guzman | A61B 17/142 |
| 2020/0375609 A1 * | 12/2020 | Miyatani | A61B 17/1604 |

FOREIGN PATENT DOCUMENTS

| | | |
|---|---|---|
| WO | 2005-104964 A1 | 11/2005 |
| WO | 2014-207552 A1 | 12/2014 |

* cited by examiner

BONE RESECTION APPARATUS

PRIORITY CLAIM AND INCORPORATION BY REFERENCE

This application claims benefit of priority under 35 USC 119(a)-(d) to Japanese Patent Application No 2019-98176, entitled "Bone Resection Apparatus", filed 27 May 2019, the content of which is incorporated herein in its entirety by reference.

FIELD OF THE INVENTION

The present invention relates to a bone resection apparatus for resecting a portion of a bone.

BACKGROUND

Knee arthroplasty may be carried out as a treatment method for knee osteoarthritis. When performing knee arthroplasty, it may be necessary to resect the bone portions that are to be replaced and to secure the artificial knee joint to the resected surfaces. In this regard, a bone cutting blade may be used as a bone resection apparatus for resection of bone.

However, during knee arthroplasty, high precision is demanded at the junction between the bones and the artificial knee joint, and it is often the case following initial resection of bones by cutting or the like that further resection of resected surfaces by additional amounts in increments on the order of 1 mm is required.

Whereas the bone cutting blade might itself be used, or a chisel or file might be used, to carry out additional resection of bones by an amount of small magnitude, as a high degree of skill is required to carry out additional resections of precise magnitude, this would place a large burden on the physician.

There is therefore a need for a bone resection apparatus that would make it possible to carry out additional resection of a resected surface of a bone easily and with high precision.

SUMMARY OF INVENTION

One aspect of the present invention is a bone resection apparatus for carrying out cutting of bone. A bone resection apparatus in accordance with one embodiment comprises a roughly planar blade body that has a tip saw blade and that carries out cutting of the bone with which the tip saw blade makes contact as a result of high-speed oscillation; and a guide plate which has a roughly planar tip guide portion, which is located at a top side of the blade body, and which is connected in such fashion as to permit sliding in the front-and-back direction relative to the blade body, the guide plate being capable of sliding between a protruding guide state in which the tip guide portion is made to protrude toward the tip to a point beyond the tip saw blade of the blade body to cover the tip saw blade and to guide a location in a thickness direction at which cutting by the tip saw blade occurs, and a retracted position at which the tip guide portion is retracted to a point behind the tip saw blade.

Another aspect of the present invention is a guide plate which when used is mounted on a roughly planar blade body that has a tip saw blade and that carries out cutting of a bone with which the tip saw blade makes contact as a result of high-speed oscillation. A guide plate in accordance with one embodiment comprises a roughly planar tip guide portion; and slide rails that hold the blade body therebetween from a top side thereof; wherein the guide plate is connected in such fashion as to permit sliding in a front-and-back direction relative to the blade body between a protruding guide state in which the tip guide portion is made to protrude toward the tip to a point beyond the tip saw blade of the blade body to cover the tip saw blade and to guide a location in a thickness direction at which cutting by the tip saw blade occurs, and a retracted guide state in which the tip guide portion is retracted to a point behind the tip saw blade; and wherein a window opening for viewing the tip saw blade from above when the tip guide portion is in the protruding guide state is formed at the tip guide portion.

Bone resection apparatuses and/or guide plates in accordance with aspects and embodiments of the present invention may make it possible to cause additional resection of small magnitude to be carried out at a resected surface of a bone easily and with high precision.

Other embodiments, systems, methods, and features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

EMBODIMENTS FOR CARRYING OUT INVENTION

Bone resection apparatuses associated with embodiments of the present invention are described in detail below with reference to the drawings. In accordance with the present embodiment, in the context of knee arthroplasty, bone resection apparatus 1 is used when carrying out further resection, by prescribed additional thickness(es) (1 mm in the present embodiment), of resected surface(s) of bone(s) at location(s) to be replaced.

Bone resection apparatus 1 in accordance with the present embodiment is an apparatus that may be used by mounting it on a bone saw hand grip 6 which is a high-speed electric oscillatory device (e.g., 10,000 revolutions per minute). In accordance with the present embodiment, bone resection apparatus 1 is provided with blade body 10, and guide plate 20 which is located at the top side of blade body 10 and which is for causing the location at which cutting by blade body 10 occurs to be guided in the thickness direction.

Figure 3:
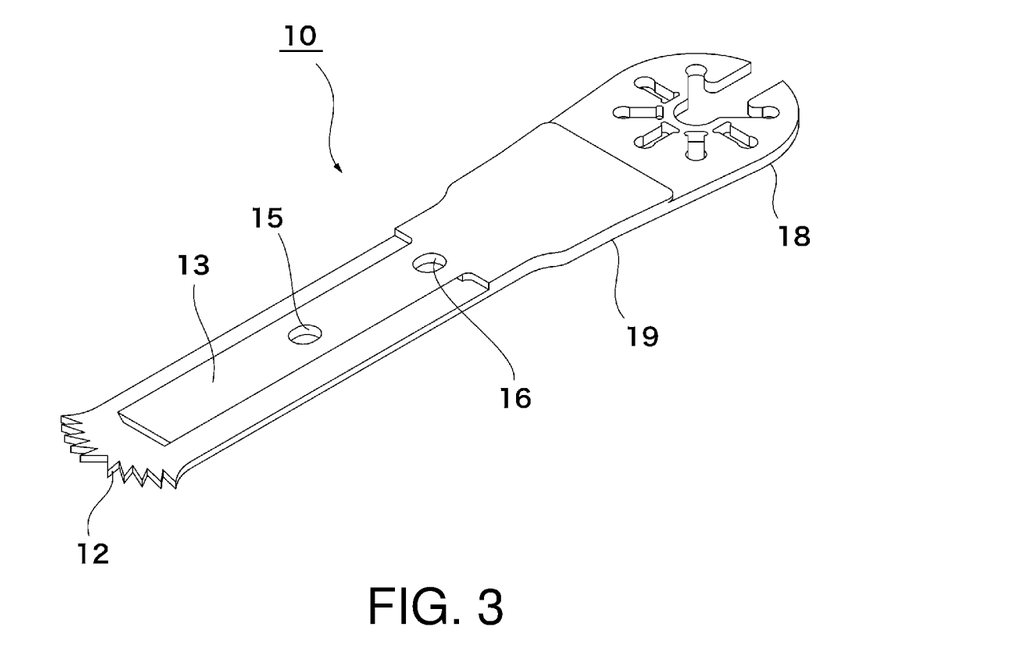
FIG. 3 is a perspective view of a blade body associated with an embodiment of the present invention as seen from above.
Figure 4:
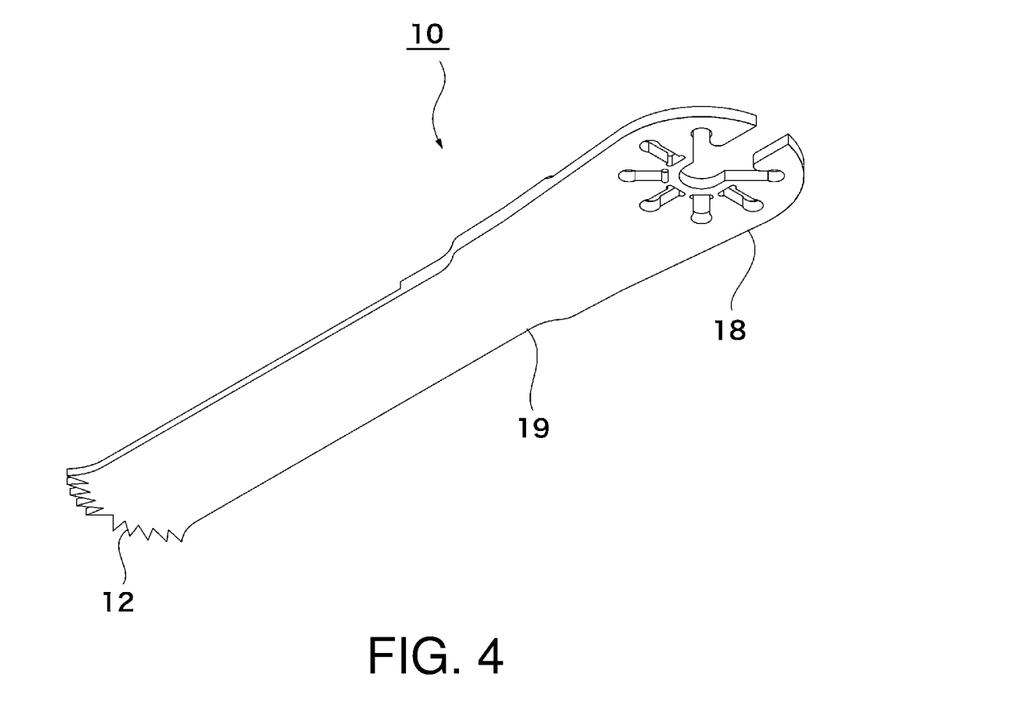
FIG. 4 is a perspective view of a blade body associated with an embodiment of the present invention as seen from below.

Blade body 10 of the present embodiment is roughly strip-like and planar, and is provided with tip saw blade 12 which is formed at the tip edge in the long direction thereof, sliding raised connector 13 which is formed at the top surface thereof and which serves as connector for connection with guide plate 20, and linking portion 18 which is formed at the back end portion thereof (portion toward an operator who holds hand grip 6) and which serves as connector for connection with hand grip 6.

In accordance with the present embodiment, the tip edge of blade body 10 is arcuate, being convex toward the tip end thereof, and tip saw blade 12 is formed so as to be arcuate in shape. When blade body 10 engages in high-speed oscillation in its width direction, i.e., in the direction in which tip saw blade 12 extends, bone at the location contacted by tip saw blade 12 is cut.

Sliding raised connector 13 of the present embodiment extends from the back end portion of tip saw blade 12 of blade body 10 to the portion toward an operator who holds hand grip 6, so as to protrude upwardly at a central region in the width direction. In an exemplary embodiment, the width of sliding raised connector 13 might be on the order of half of the width of blade body 10. In an exemplary embodiment, the thickness of sliding raised connector 13 might be the same as the thickness (1 mm) of tip saw blade 12, and the thickness of blade body 10 at the location corresponding to sliding raised connector 13 might be two times (2 mm) that which exists at the location corresponding to tip saw blade 12.

Formed at either side edge of sliding raised connector 13 of the present embodiment there may be notches inclined in such direction as to cause the width thereof to decrease as one proceeds toward the bottom thereof, matable insertion of the two side edges of this sliding raised connector 13 between slide rails 29 of guide plate 20, described below, permitting sliding raised connector 13 to be held in slidable fashion between slide rails 29.

In accordance with the present embodiment, linking portion 18 is the portion that is secured to hand grip 6. In an exemplary embodiment, thickness of linking portion 18 might be 1.5 mm, which in the present example is greater than the thickness at the portion corresponding to tip saw blade 12 but less than the thickness at the portion corresponding to sliding raised connector 13.

In accordance with the present embodiment, thick portion 19, which in the present example might be of the same thickness (2 mm) as the portion corresponding to sliding raised connector 13, is disposed between sliding raised connector 13 and linking portion 18. Thick portion 19 of the present embodiment is provided along the entire width of blade body 10.

In an embodiment in which blade body 10 is long, slender, and planar in shape, causing this to be driven by hand grip 6, and to engage in high-speed oscillation in the width direction during cutting, especially where a thin blade body 10 of low flexural rigidity is employed, may result in a situation in which high-speed oscillation causes occurrence of bending such that the tip portion thereof moves in the vertical direction, as a result of which there could be reduction in cutting precision. On the other hand, increasing the thickness of the entire blade body 10 in accordance with another embodiment so as to increase flexural rigidity may cause the weight of blade body 10 to increase, as a result of which it may be difficult to cause high-speed oscillation to occur in stable fashion.

But where as in the present embodiment a thick portion 19 and a sliding raised connector 13 of suitable thickness are disposed toward a central region in the long direction of blade body 10, it will be possible by increasing the flexural rigidity of blade body 10 to prevent occurrence of bending and to achieve cutting with high precision while suppressing increase in the overall weight thereof.

In one embodiment, lock holes 15, 16 may be formed at two prescribed locations in the long direction at the portion of sliding raised connector 13 corresponding to a central region in the width direction of blade body 10. These lock holes 15, 16 may be used to secure the positional relationship between guide plate 20 and blade body 10 which when not secured in such fashion might be capable of being changed as a result of relative sliding therebetween. In a preferred embodiment, lock holes 15, 16 do not go all the way through blade body 10 but extend to a depth of, for example, 1 mm, preferably being formed so as to only be present at portions corresponding to sliding raised connector 13.

Figure 1:
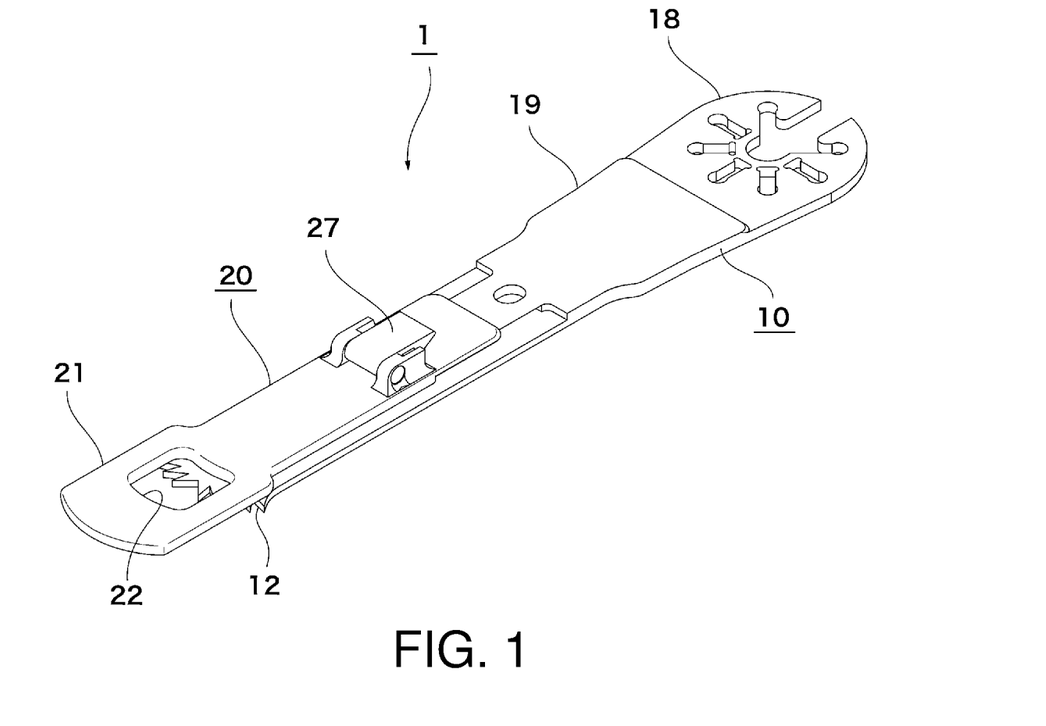
FIG. 1 is a perspective view of a bone resection apparatus associated with an embodiment of the present invention as seen from above.
Figure 2:
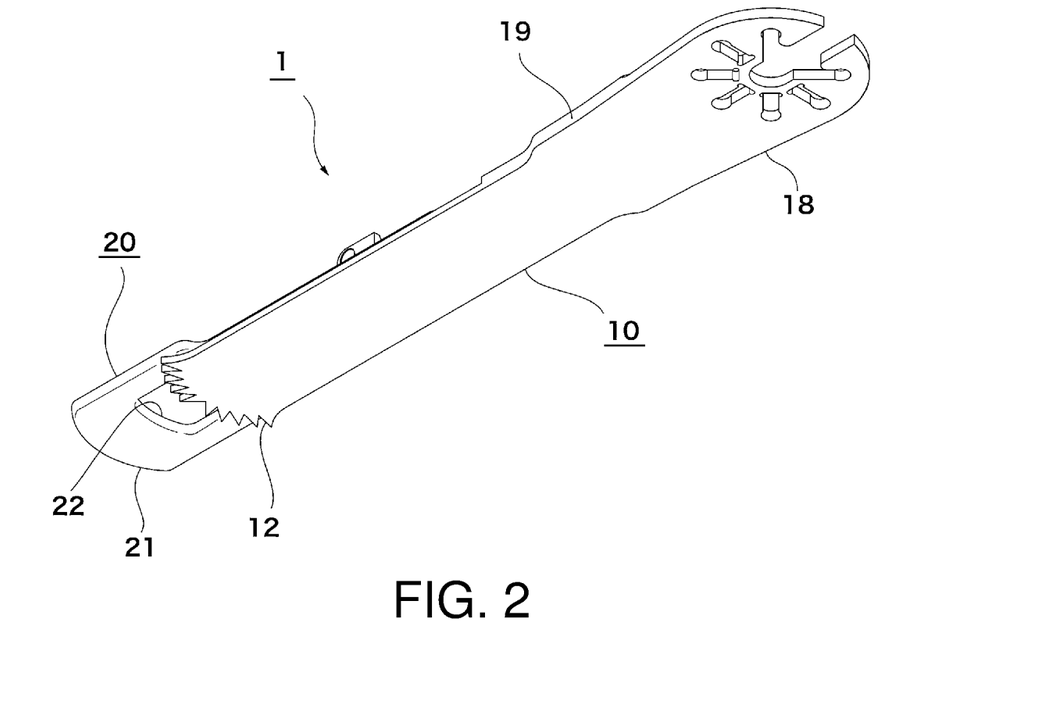
FIG. 2 is a perspective view of a bone resection apparatus associated with an embodiment of the present invention as seen from below.
Figure 7:
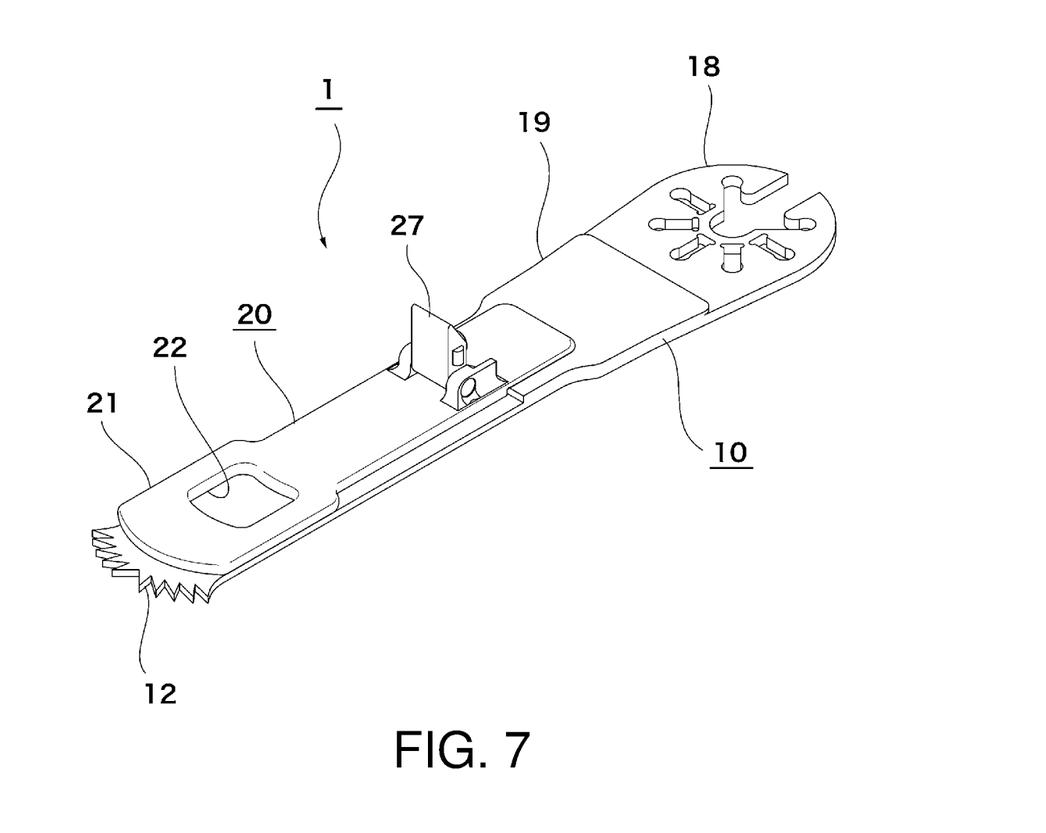
FIG. 7 is a perspective view of a bone resection apparatus associated with an embodiment of the present invention as seen from above.

In such an embodiment, first lock hole 15 is preferably a hole permitting guide plate 20 to be secured in a protruding guide state relative to blade body 10, in which state the tip end of guide plate 20 is preferably made to protrude toward the front to a point beyond the tip edge of blade body 10 and act as guide; and second lock hole 16 is preferably a hole permitting guide plate 20 to be secured in a retracted guide state relative to blade body 10, in which state the tip end of guide plate 20 is preferably retracted from the tip edge of blade body 10 and does not act as guide. Bone resection apparatus 1 in accordance with such an embodiment is shown in FIG. 1 and FIG. 2 with guide plate 20 secured in the protruding guide state relative to blade body 10, and is shown in FIG. 7 with guide plate 20 secured in the retracted guide state relative to blade body 10.

Figure 5:
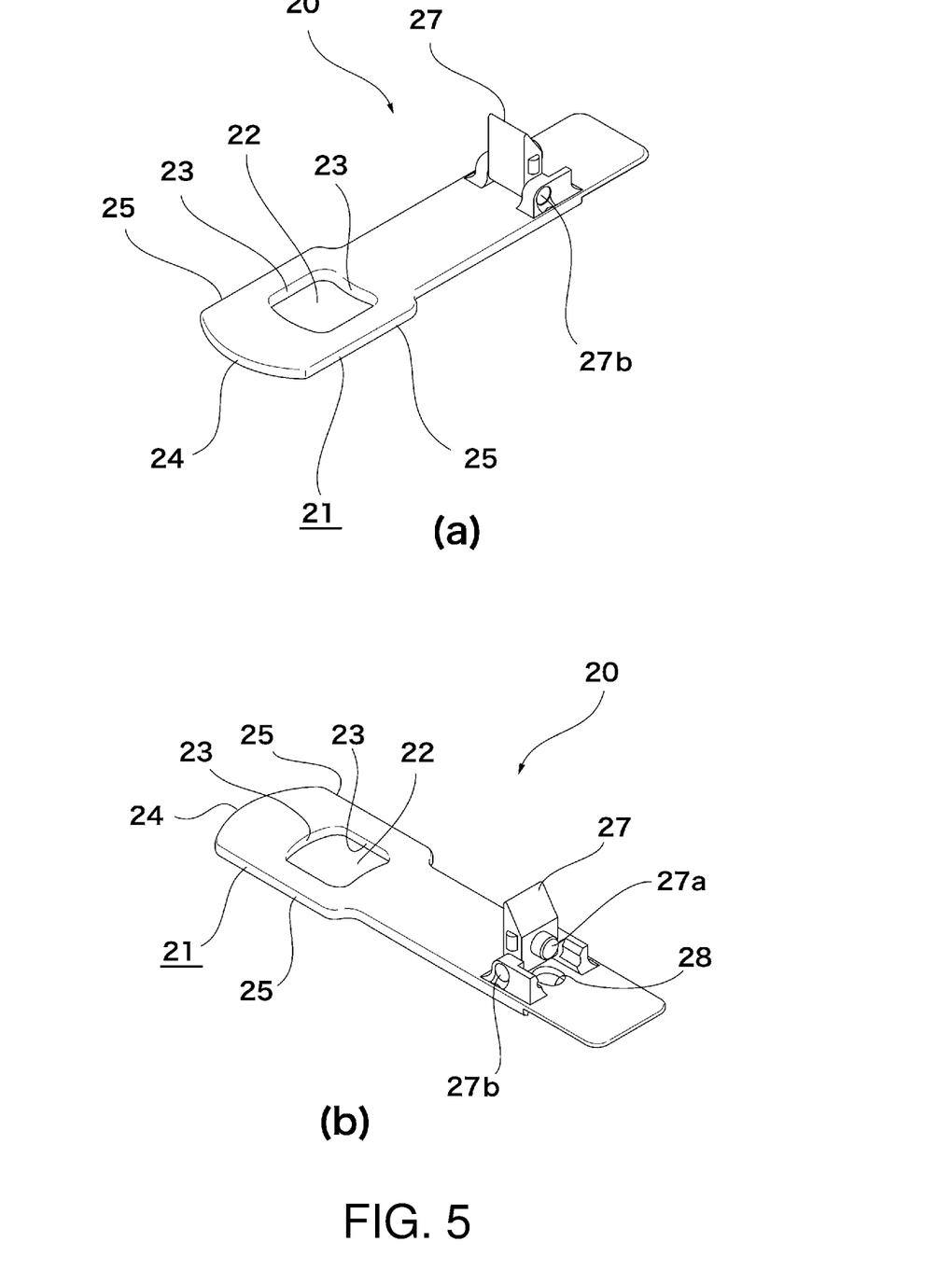
FIG. 5 is a perspective view of a guide plate associated with an embodiment of the present invention as seen from above.
Figure 6:
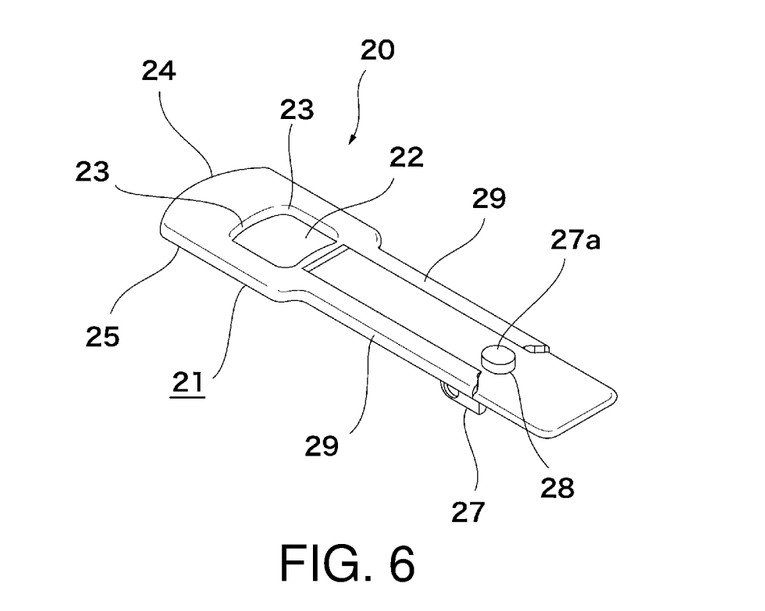
FIG. 6 is a perspective view of a guide plate associated with an embodiment of the present invention as seen from below.

In a preferred embodiment, guide plate 20 is roughly strip-like and planar, its width preferably being roughly the same as that of blade body 10, and its length in the long direction thereof preferably being on the order of approximately three-fifths that of blade body 10. In one embodiment, guide plate 20 is provided with tip guide portion 21 which is disposed at the tip portion thereof, pivoting lock 27 which is disposed at the top surface thereof, and slide rails 29 which are disposed so as to extend in the long direction at the bottom surface thereof.

In a preferred embodiment, tip guide portion 21 is a rectangular plate-like component preferably occupying a region on the order of one-fourth of guide plate 20 at a region toward the tip end thereof, and is preferably provided with rectangular window opening 22 at a location in the central portion thereof. Each of the two sides of window opening 22 that extend in the width direction, i.e., the side toward the tip end and the side toward the back end, may be arcuate, being convex toward the tip end thereof.

By forming window opening 22 at the tip portion of guide plate 20, it will be possible to observe tip saw blade 12 from a location above blade body 10 by way of window opening 22, and it will also be possible by way of window opening 22 to cause bone chips produced as a result of cutting by tip saw blade 12 to be expelled therefrom and so forth.

In one embodiment, the outer peripheral edge of tip guide portion 21 comprises radiused surfaces 24, 25, tip edge radiused surface 24 being formed at the tip portion thereof, and outside edge radiused surfaces 25 being formed at either side portion thereof. By thus causing the outer periphery of tip guide portion 21 to comprise radiused surfaces 24, 25, it is possible to prevent occurrence of a situation in which the outer edge of tip guide portion 21, which engages in high-speed oscillation in the width direction during cutting, might otherwise come in contact with bone, as a result of which there might be occurrence of chipping of bone or interference with ability to engage in smooth high-speed oscillation due to friction.

Furthermore, in a preferred embodiment, inside edge radiused surface 23 is formed at the inside side faces of window opening 22. By thus forming inside edge radiused surface 23 thereat, not only will it be possible to cause the high-speed oscillation in the width direction of tip guide portion 21 to proceed in smooth fashion, but it will also be possible, where bone chips produced by cutting are in a moist state, to prevent a situation in which bone chips might otherwise successively clump together in lumps within window opening 22 before being expelled therefrom, as a result of which bone chips might be scattered thereabout.

It is preferred, at least where oscillation occurs in the width direction, that this inside edge radiused surface 23 of window opening 22 be formed at the two sides that are to either side thereof and that extend in the long direction which is perpendicular to the direction of oscillation, and it is further preferred as in the present embodiment that it be formed at all four sides including the two sides thereof that extend in the width direction.

In accordance with one embodiment, pivoting lock 27 may be disposed at the top surface of guide plate 20, and may be provided with pivot shaft 27b which is horizontal, being parallel to the width direction; and with cylindrical projection 27a, which is capable of pivoting about this pivot shaft 27b. Cylindrical projection 27a may be capable of pivoting between a locked position, at which it protrudes from the bottom of guide plate 20 by way of lock hole 28 formed in guide plate 20; and an unlocked position, at which it is retracted upwardly from the locked position.

In such an embodiment, when in the locked position, engagement of cylindrical projection 27a with first lock hole 15 or second lock hole 16 preferably causes blade body 10 and guide plate 20 to be secured in such fashion as to prevent relative sliding therebetween; and when in the unlocked position, disengagement of cylindrical projection 27a from first lock hole 15 and second lock hole 16 preferably makes it possible for sliding to occur between blade body 10 and guide plate 20.

In a preferred embodiment, slide rails 29 are disposed so as to extend in the long direction at either edge portion at the bottom surface of guide plate 20, the two side edges of the aforementioned sliding raised connector 13 preferably being held in slidable fashion between slide rails 29. In such an embodiment, slide rails 29 preferably extend from a portion of tip guide portion 21 at the end toward an operator who holds hand grip 6 to the location at which pivoting lock 27 is disposed near the back end of guide plate 20.

In a preferred embodiment, guide plate 20 is such that whereas the portion corresponding to tip guide portion 21 is of roughly the same width as blade body 10, the width of the portion which is toward the back end thereof from tip guide portion 21 is narrower, the size thereof being such that the width thereat is slightly greater than that of sliding raised connector 13 of blade body 10.

Description of the constitution of bone resection apparatus 1 having been given above, a manner of using bone resection apparatus 1 will now be described in the context of an example in which the resected plane of a bone is subjected to adjustment by carrying out further cutting of an additional 1 mm thereat. In a preferred embodiment, bone resection apparatus 1 is used by causing linking portion 18 to be secured to the connecting portion of hand grip 6, driving by hand grip 6 causing blade body 10 to oscillate at high speed in the width direction.

Figure 8:
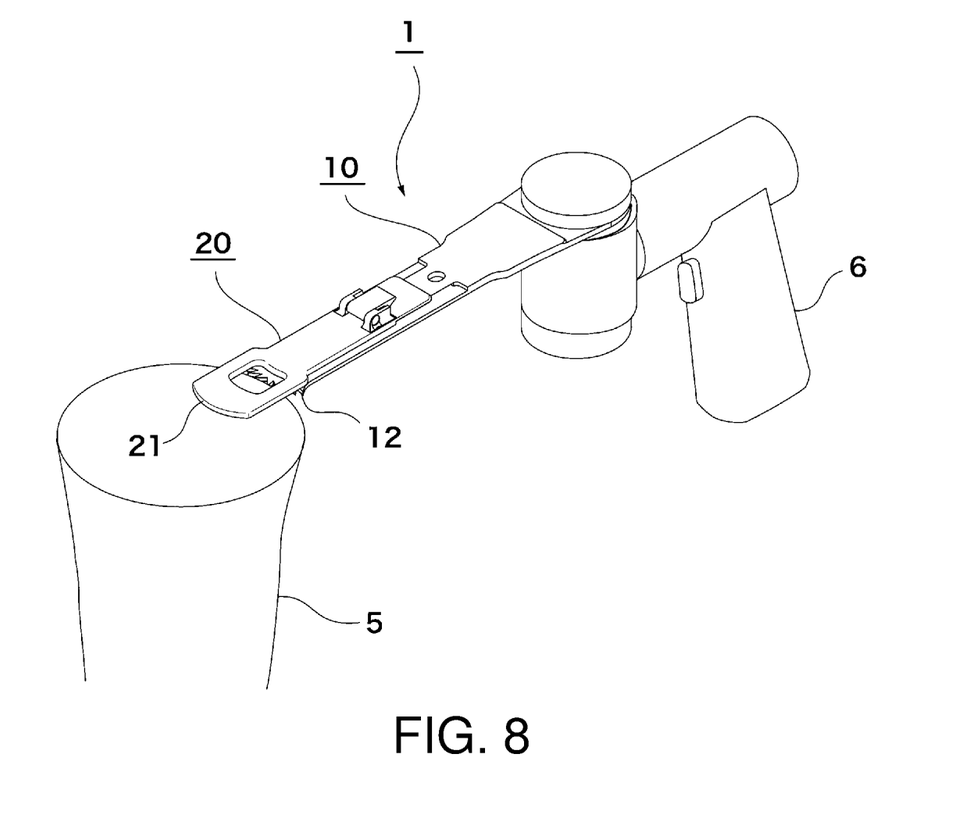
FIG. 8 is a perspective view showing a bone resection apparatus associated with an embodiment of the present invention while it is in use.
Figure 9:
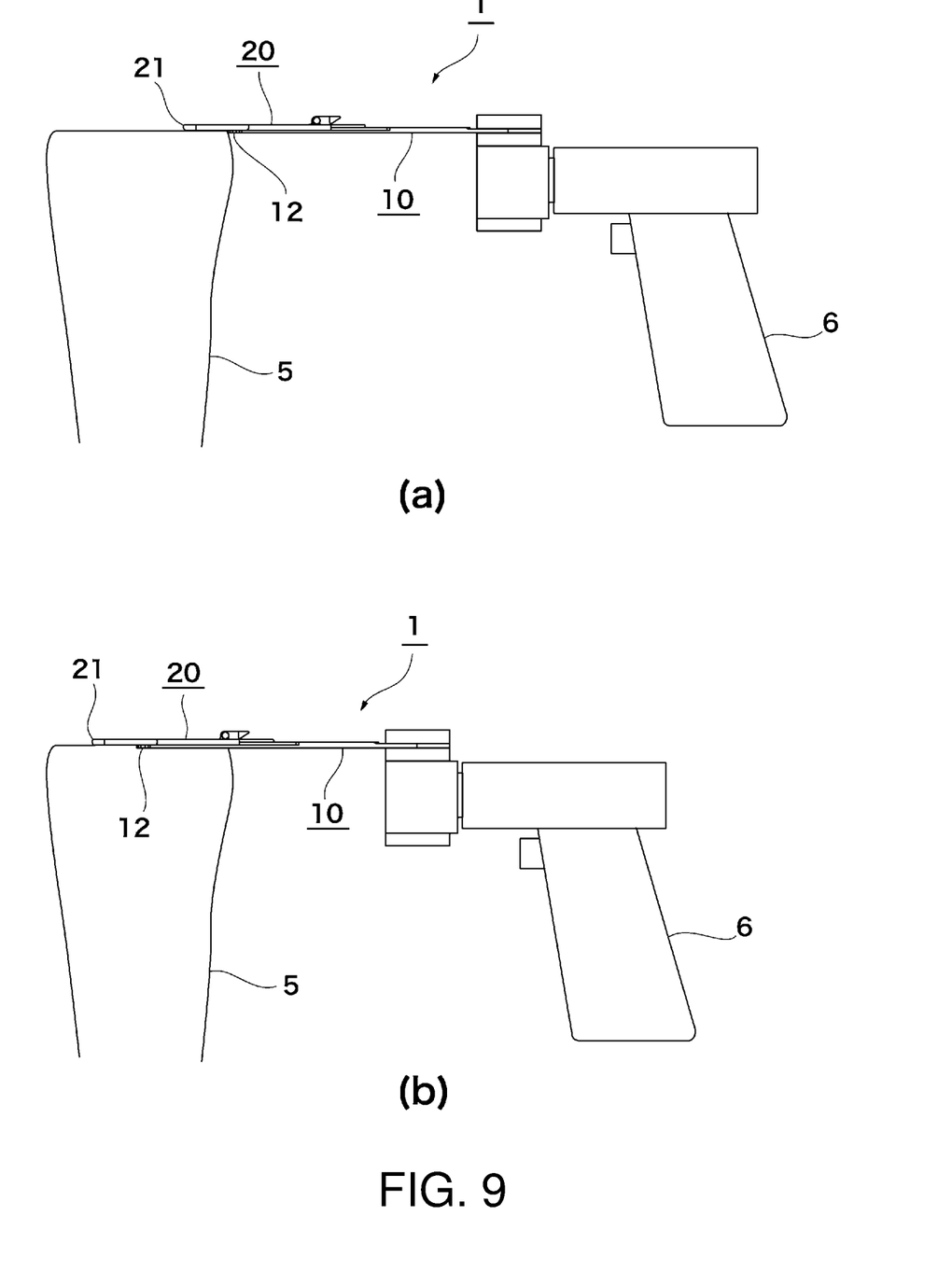
FIG. 9 is a side view showing a bone resection apparatus associated with an embodiment of the present invention while it is in use.
Figure 10:
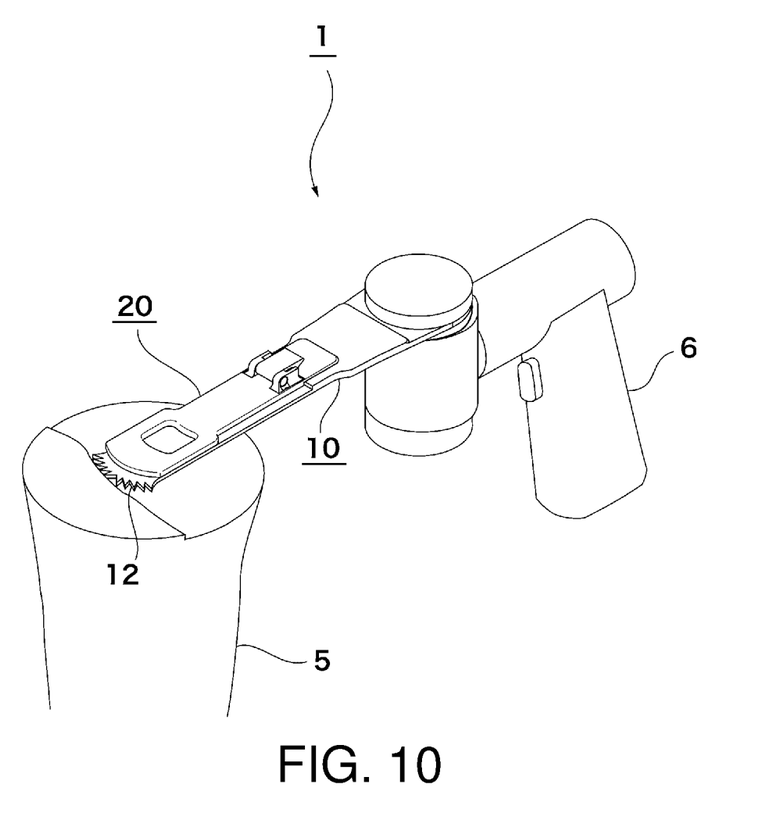
FIG. 10 is a perspective view showing a bone resection apparatus associated with an embodiment of the present invention while it is in use.

FIG. 8 shows the situation that exists when beginning to carry out resection by bone resection apparatus 1 in accordance with a preferred embodiment. (a) at FIG. 9 also shows the situation that exists when beginning to carry out resection by bone resection apparatus 1 of such an embodiment, and (b) at FIG. 9 shows the situation that exists when an additional portion that is on the order of seven-tenths of the resected surface has been resected therefrom. FIG. 10 shows the situation that exists when guide plate 20 in accordance with a preferred embodiment is secured in the retracted guide state, in which state cutting of the remainder of the resected surface would be carried out without use of the guide.

As shown at FIG. 8 and at (a) in FIG. 9, when beginning to carry out resection, the positional relationship between guide plate and 20 blade body 10 of bone resection apparatus 1 in accordance with the embodiment shown would be secured in the protruding guide state, in which state tip guide portion 21 of guide plate 20 is preferably made to protrude toward the tip end thereof to a point beyond the tip of blade body 10. The securing at this positional relationship might, for example, be achieved by causing cylindrical projection 27a of pivoting lock 27 to be inserted in and secured to first lock hole 15.

When beginning to carry out resection, bone resection apparatus 1 of the present embodiment would be secured in the protruding guide state and would be placed in a resection start position which is such that the bottom surface of tip guide portion 21 makes contact in parallel fashion with the resected surface of bone 5, and which is such that tip saw blade 12 of blade body 10 comes in contact with the side face at the top end portion of bone 5.

While in this state, when hand grip 6 is driven and bone resection apparatus 1 is made to engage in high-speed oscillation to the left and to the right in the width direction, bone 5 will be cut at the location that is contacted by tip saw blade 12. Moreover, in the embodiment shown, by pushing hand grip 6 forward while pressing guide plate 20 against the resected surface, the operator can cause tip saw blade 12 to be pushed further toward the tip and can cause the top end portion of bone 5 to be successively cut from the side.

By thus causing the operation to proceed while pressing this thereagainst in such fashion that the bottom surface of tip guide portion 21 of guide plate 20 always makes contact in parallel fashion with the resected surface of bone 5, in accordance with the present embodiment the operator can cause tip saw blade 12 to be such that the position thereof in the thickness direction is guided in such fashion as to always be located in a region that is 1 mm in a downward direction from the initial location of the resected surface, and can cause a thickness corresponding to the thickness (1 mm) of tip saw blade 12 to be successively additionally resected from the end of the resected surface of bone 5 (see (b) at FIG. 9).

Furthermore, at this time, as chips of resected bone 5 successively collect and clump together in lumps as they impact the inside edges to the left and to the right within window opening 22 at high speed, they will in a preferred embodiment as has been described above be successively expelled to the exterior.

Thus, as shown at (b) in FIG. 9, a new resected surface, which is one level lower than the original resected surface, will in accordance with the present embodiment be formed at the region that is newly cut by tip saw blade 12. In accordance with the present embodiment, the step, i.e., difference in height, between the original resected surface and the new resected surface will in general correspond to the thickness of tip saw blade 12, which is approximately 1 mm in the present embodiment.

As the original resected surface is trimmed away and becomes smaller, a point may be reached where it is no longer possible to press guide plate 20 thereagainst; and when the new resected surface which is one level lower reaches a certain size, a point may be reached where, by causing cutting to be carried out as the bottom surface of blade body 10 is pressed against the new resected surface and contact is made therewith in parallel fashion, it becomes possible, even without being guided by guide plate 20, to cut away and remove what remains of the original resected surface (see FIG. 10).

For example as shown at (b) in FIG. 9, after on the order of seven-tenths of the resected surface has been cut away as viewed from the side, it will be possible even without being guided by guide plate 20 to cut what remains of the original resected surface to a 1 mm thickness.

In a preferred embodiment, it will therefore be possible to cause the positional relationship between guide plate 20 and blade body 10 of bone resection apparatus 1 to be secured in the retracted guide state, and to use tip saw blade 12 of blade body 10 to cut away the remaining portion of the original resected surface without being guided by guide plate 20.

As described above, in accordance with the present embodiment, even where it is desired that a resected surface of a bone 5 be further resected by an additional amount of small magnitude, by causing the positional relationship between guide plate 20 and blade body 10 to be secured in the protruding guide state, and by carrying out resection by tip saw blade 12 of blade body 10 while being guided by tip guide portion 21, it will be possible to accurately carry out additional resection.

Furthermore, in accordance with the present embodiment, by causing the positional relationship between guide plate 20 and blade body 10 to be secured in the retracted guide state, it will be possible, without going to the trouble of removing guide plate 20, to use tip saw blade 12 of blade body 20 to carry out resection without being guided by guide plate 20.

Furthermore, in accordance with the present embodiment, as a result of formation of window opening 22, it will be possible to carry out cutting while monitoring the status of tip saw blade 12, and it will be possible to cause chips of bone 5 produced by cutting to be expelled to the exterior by way of window opening 22, making it possible to prevent occurrence of a situation in which bone chips accumulate and impede cutting.

Figure 11:
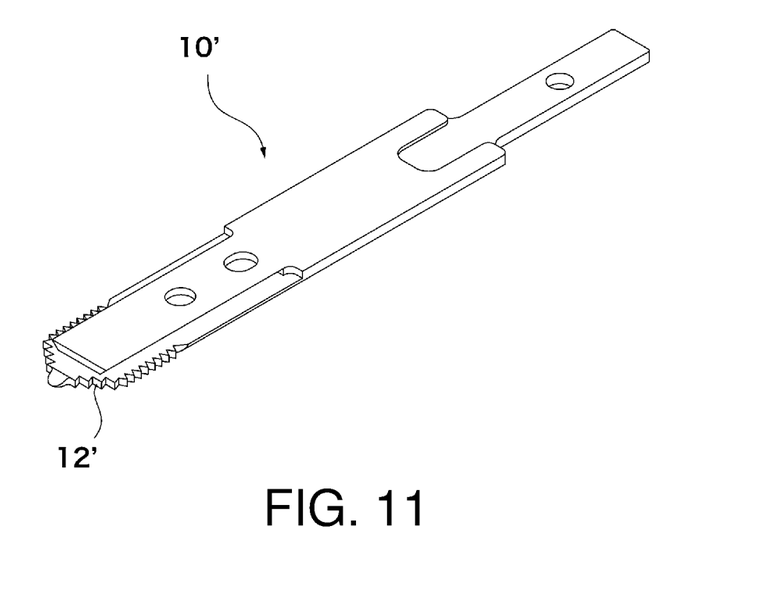
FIG. 11 is a perspective view of a blade body associated with a variation on an embodiment of the present invention as seen from above.

Variations on the present embodiment will now be described with reference to FIG. 11 and FIG. 12. FIG. 11 shows a variation on blade body 10. Whereas in the foregoing embodiment tip guide portion 21 carries out cutting of bone with which it makes contact as a result of high-speed oscillation of blade body 10 in the width direction, blade body 10' associated with the present variation differs therefrom with respect to the fact that it is provided with tip saw blade 12' formed at the edge faces to either side and at the tip side face of the tip portion thereof, and with respect to the fact that tip saw blade 12' carries out cutting of bone with which it makes contact as a result of high-speed oscillation of blade body 10' in the front-and-back direction.

Blade body 10' having such constitution will also permit employment of guide plate 20, and will provide operation and effect similar to those of the foregoing embodiment.

Figure 12:
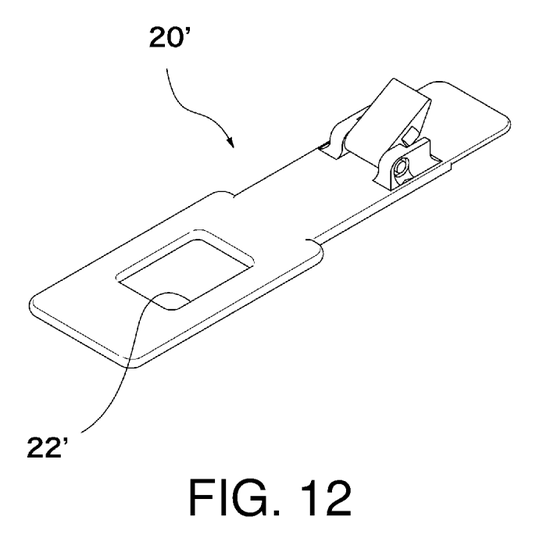
FIG. 12 is a perspective view of a guide plate associated with a variation on an embodiment of the present invention as seen from above.

FIG. 12 shows a variation on the guide plate. Guide plate 20' associated with the present variation differs with respect to the fact that window opening 22' is more nearly in the shape of an square than is the case in the foregoing embodiment. The window opening may of course be circular or elliptical in shape. Guide plate 20' associated with the present variation will also provide operation and effect similar to those of the foregoing embodiment.

While embodiments of the present invention including variations thereon have been described above, the present invention is not limited to the embodiments that have been described above, a great many variations being possible without departing from the gist of the present invention. For example, the shapes, sizes, materials, and so forth of the parts from which the bone resection apparatus is formed may be varied as appropriate.

Furthermore, bone resection apparatuses associated with the present embodiment are not limited to knee arthroplasty but may be employed in a wide variety of situations in which additional resection of all or any portion of a resected surface of a bone is to be carried out.

EXPLANATION OF REFERENCE NUMERALS

1 Bone resection apparatus
10 Blade body
12 Tip saw blade
13 Sliding raised connector
15 First lock hole
16 Second lock hole
18 Linking portion
19 Thick portion
20 Guide plate
21 Tip guide portion
22 Window opening
23 Inside edge radiused surface
24 Tip edge radiused surface
25 Outside edge radiused surfaces
27 Pivoting lock
27a Cylindrical projection 27b Pivot shaft
28 Lock hole
29 Slide rail
5 Bone
6 Hand grip

What is claimed is:

1. A bone resection apparatus for carrying out cutting of a bone, the bone resection apparatus comprising:
 a roughly planar blade body that has a tip saw blade and that carries out cutting of the bone with which the tip saw blade makes contact as a result of high-speed oscillation; and
 a guide plate which has a roughly planar tip guide portion, which is located at a top side of the blade body, and which is connected in such fashion as to permit sliding in a front-and-back direction relative to the blade body, the guide plate being capable of sliding between a protruding guide state in which the tip guide portion is made to protrude toward the tip to a point beyond the tip saw blade of the blade body to cover the tip saw blade and to guide a location in a thickness direction at which cutting by the tip saw blade occurs, and a retracted guide state in which the tip guide portion is retracted to a point behind the tip saw blade.

2. The bone resection apparatus according to claim 1 wherein formed at the tip guide portion there is a window opening for viewing the tip saw blade from above when the tip guide portion is in the protruding guide state.

3. The bone resection apparatus according to claim 2 wherein an inside side face of the window opening of the tip guide portion is a radiused surface.

4. The bone resection apparatus according to claim 1 wherein an outside side face of the tip guide portion is a radiused surface.

5. The bone resection apparatus according to claim 1 wherein
 the blade body has a sliding raised connector that protrudes from a top surface thereof in such fashion as to extend in the front-and-back direction; and
 the guide plate has slide rails disposed at a bottom surface thereof that hold the sliding raised connector therebetween from the top side thereof.

6. The bone resection apparatus according to claim 1 wherein the guide plate further has a lock for causing the guide plate to be secured in the protruding guide state or the retracted guide state.

7. A bone resection apparatus comprising a blade body and a guide plate which when used is mounted on the blade body, the blade body being roughly planar, having a tip saw blade, and carrying out cutting of a bone with which the tip saw blade makes contact as a result of high-speed oscillation, wherein the guide plate comprises:
 a roughly planar tip guide portion; and
 slide rails that hold the blade body therebetween from a top side thereof;
 wherein the guide plate is connected in such fashion as to permit sliding in a front-and-back direction relative to the blade body between a protruding guide state in which the tip guide portion is made to protrude toward a tip to a point beyond the tip saw blade of the blade body to cover the tip saw blade and to guide a location in a thickness direction at which cutting by the tip saw blade occurs, and a retracted guide state in which the tip guide portion is retracted to a point behind the tip saw blade; and
 wherein a window opening for viewing the tip saw blade from above when the tip guide portion is in the protruding guide state is formed at the tip guide portion.

* * * * *